United States Patent [19]
Yland et al.

[11] Patent Number: 5,326,706
[45] Date of Patent: Jul. 5, 1994

[54] HOMEOSTATIC ORGAN PRESERVATION SYSTEM

[75] Inventors: Marc J. Yland, E. Setauket, N.Y.; David Anaise, El Paso, Tex.

[73] Assignee: Research Foundation of State University of New York, Albany, N.Y.

[21] Appl. No.: 576,058

[22] Filed: Aug. 31, 1990

Related U.S. Application Data

[63] Continuation-in-part of Ser. No. 380,870, Jul. 17, 1989, abandoned.

[51] Int. Cl.$^5$ .................... A01N 1/02; C12M 1/36; A61N 1/30; A61M 1/00
[52] U.S. Cl. .................... 435/283; 435/1; 435/2; 435/289; 604/19; 604/31
[58] Field of Search ............. 435/1, 2, 283, 287, 435/289, 290, 311, 313; 604/19, 21, 22, 27, 31

[56] References Cited

U.S. PATENT DOCUMENTS

| | | | |
|---|---|---|---|
| 3,064,649 | 11/1962 | Fuson | 96/205 |
| 3,406,531 | 10/1968 | Swenson et al. | 62/306 |
| 3,490,438 | 1/1970 | Lavender et al. | 128/1 |
| 3,545,221 | 12/1970 | Swenson | 62/231 |
| 3,632,473 | 1/1972 | Belzev | 435/1 |
| 3,660,241 | 5/1972 | Michielsen | 195/127 |
| 3,753,865 | 8/1973 | Belzer et al. | 195/400 |
| 3,911,898 | 10/1975 | Leachman, Jr. | 128/10 |
| 3,995,444 | 12/1976 | Clark | 62/306 |
| 4,186,565 | 2/1980 | Toledo-Pereyva | 62/306 |
| 4,192,302 | 3/1980 | Boddie | 128/214 R |
| 4,416,280 | 11/1983 | Carpenter et al. | 128/399 |
| 4,427,009 | 1/1984 | Wells et al. | 607/106 |
| 4,466,777 | 8/1984 | Kimberlin | 417/12 |
| 4,473,637 | 9/1984 | Guibert | 435/1 |
| 4,476,867 | 10/1984 | Parks | 128/400 |
| 4,666,425 | 5/1987 | Fleming | 604/4 |
| 4,762,794 | 8/1988 | Nees | 435/284 |
| 4,837,390 | 6/1989 | Reneau | 435/1 |

FOREIGN PATENT DOCUMENTS 908363  2/1982  U.S.S.R. .................... A61M 1/00

OTHER PUBLICATIONS

Kachelhoffer, et al. Eur. Surg. Res. 8:461–470 (1976).
Toledo-Pereyra et al The American Surgeon 50:493–495 (1984).
Mavroudis, The Annals of Thoracic Surgery 25:3:259–271 (1978).
Collins et al Cryobiology 21:1–5 (1984).
(List continued on next page.)

Primary Examiner—Michael G. Wityshyn
Assistant Examiner—Jane Williams
Attorney, Agent, or Firm—Hoffmann & Baron

[57] ABSTRACT

A homeostatic organ preservation system includes structure for defining a chamber for holding a donor organ, and a pump for providing a perfusion solution to the organ. A first conduit is coupled to the pump and is adapted to be coupled to the organ. The first conduit provides perfusion solution from the pump to the organ. A second conduit is coupled to the pump and to the organ chamber. The second conduit returns perfusion solution from the organ chamber to the pump. A pressure sensor is coupled to the first conduit to sense the pressure of the perfusion solution in the first conduit. The pressure sensor provides an output signal which is indicative of the vascular resistance of the organ. A pump control circuit is also included. The pump control circuit is responsive to the output signal of the pressure sensor to raise and lower the pump pulse rate respectively in response to a decrease and increase in the organ vascular resistance. A method of perfusing the donor organ, in which the organ is placed in the chamber and connected to a conduit which, in turn, is connected to a pump, includes the steps of monitoring the pressure of the perfusion solution in the conduit, and adjusting the pump pulse rate in accordance with the pressure of the perfusion solution. The pulse rate of the pump is decreased if the resistance of the perfused organ increases, and will be increased if the resistance of the perfused organ decreases.

20 Claims, 6 Drawing Sheets

OTHER PUBLICATIONS

Tokunaka et al. Transplantation 45:1031–1035 (1988).

Rice et al. Cryobiology 22:161–167 (1985).

*Perfusion Nephropathy In Human Transplants,* the New England Journal of Medicine, vol. 295, No. 22, Nov. 25, 1976, pp. 1217–1221.

*Structural Injury Produced by Pulsatile Perfusion vs. Cold Storage Renal Preservation,* in Surgical Forum, undated, pp.313–315.

*Preservation of Canine Kidneys,* published in Arch Surg./vol. 98, Jan., 1969, pp. 121–127.

*The Usefulness Of Initial Brief Pulsatile Perfusion In Extending The Applicability Of Cold Storage For Renal Transplantation-A Preliminary Report,* published in Transplantation Proceedings, No. 4, Oct., 1988, pages unknown.

*A Small Perfusion Apparatus For The Study of Surviving Isolated Organs,* by Long and Lyons, Journal of Laboratory and Clinical Medicine, vol. 44, No. 4, Oct., 1954, pp. 614–626.

*A Pulsating Perfusion Apparatus,* by J. S. Long, dated 1947.

HOMEOSTATIC ORGAN PRESERVATION SYSTEM

CROSS REFERENCE TO RELATED APPLICATIONS

This application is a continuation-in-part of co-pending prior application Ser. No. 07/380,870, filed Jul. 17, 1989, now abandoned.

BACKGROUND OF THE INVENTION

1. Field of the Invention

This invention relates to a homeostatic organ preservation system, and more particularly relates to a method and apparatus for perfusing an organ or the whole body of a non-heart beating cadaver. Even more specifically, the invention relates to a pump for use in an organ preservation system.

The science of organ preservation has been rapidly increasing in importance over recent years because of the increase in organ transplantation as a medical procedure. Basically, in organ preservation, an organ, such as a kidney, pancreas, liver, lung or heart, is removed from a donor and maintained in a viable condition by artificial means. This is done to maintain the organ until the recipient is selected and prepared to receive it.

Current procurement technology allows the removal of organs from brain-dead trauma victims, that is, heart-beating donors who are otherwise in good physiological state. Another source of transplantable organs is victims of motor vehicle accidents who succumb to their injuries in the emergency room or in the intensive care unit, in other words, non-heart beating donors. However, utilization of organs removed from these donor sources is limited, basically because of the time required to obtain consent from the families of the potential donors prior to retrieval of such organs and the need to secure an operating room. Accordingly, in situ flush and cooling of organs would be advantageous in such situations.

Irrespective of the source from which the donor organs are retrieved, it is important to cool the targeted organ rapidly to minimize the deleterious effects of warm ischemia to the organ's microvasculature. Usually, a rapid flush of the organ's microvasculature, which results in the rapid cooling of the organ, for example, to less than 15° C. in the case of a kidney, and removal of red blood cells from the microcirculation should be performed as soon as possible, for example, within about one half-hour in the case of a kidney, following cessation of blood flow through the organ. This rapid cooling of the organ should be followed by the maintenance of cold temperature for a given period of time while the recipient is selected and prepared to receive the organ.

2. Description of the Prior Art

Generally, current organ preservation systems incorporate a pump which is designed to deliver cold perfusate at a constant flow. During perfusion, as the organ's vascular resistance increases, the perfusion pressure increases to maintain flow. Accordingly, one of the problems with current organ preservation pumps is that they tend to damage the delicate microvasculature of the organ which, in turn, causes the microvasculature resistance to further increase. In response to this further increase in resistance, the conventional pump further increases pressure, resulting in greater tissue injury.

A typical organ preservation pump is Model No. MOX-100TMA, manufactured by Waters Instruments, Inc. of Rochester, Minn. The Waters Instruments pump, in many ways, simulates the action of the heart in providing a cold perfusion solution to a donor organ previously removed and being maintained in a viable state prior to transplantation. The pump incorporates a lever arm which compresses an elongated resilient tube. The tube is coupled to the donor organ. The frequency of compression of the lever arm is manually adjustable, but usually is set at a relatively high pulse rate, that is, about 60 beats per minute. This action causes perfusate to flow into the donor organ. In the above described Waters Instruments Company device, the donor organ is maintained in a container connected to the machine. It is the perfusion solution which cools the organ. Thus, if perfusion ceases, the organ will warm up and damage to the organ may occur.

There are also non-pulsating types of organ perfusion apparatuses. Such apparatuses provide a preset "trickle" flow of perfusate to the isolated organ. Generally, these devices do not have any feedback control of the perfusate flow rate or pressure. Without such feedback control, there is no way of determining whether the organ is being sufficiently perfused. A hypothermic isolated organ does not have the neurological connection to protect itself by constricting its vasculature under high pressure conditions, or by dilating to open its capillaries to allow more flow. Thus, without feedback control, these apparatuses may be providing perfusate to the organ at inadequate or undesirably high volumes and pressures.

Besides the problem of forcing a given volume of perfusion solution into the organ under excessive pressure, which may result in damage to the organ's microvasculature, conventional organ preservation systems generally do not allow for the low pulse rates required during hypothermic organ perfusion. Furthermore, current machines are limited to a few hours of battery power and need frequent replacement of the ice container.

In addition, currently available organ preservation machines can weigh more than 25 kilograms and are relatively large. Such machines also may cost upwardly of $15,000 or more and $500 per disposable cassette, if such is provided.

OBJECTS AND SUMMARY OF THE INVENTION

It is an object of the present invention to provide a homeostatic organ preservation system and a method and apparatus for perfusing a targeted organ which minimizes damage to the organ's microvasculature.

It is another object of the present invention to provide an organ preservation system which incorporates a pump which is adapted to operate at low pulse rates, which are preferable during hypothermic organ perfusion.

It is yet another object of the present invention to provide an organ perfusion apparatus and method, which will automatically respond to changes in vasculature resistance to prevent tissue damage to the organ.

It is a further object of the present invention to provide an apparatus and method for perfusing a donor organ, which apparatus allows for adjustments in flow, pressure, pulse rate and the differential of pressure over time over a wider range than conventional perfusion machines.

It is yet a further object of the present invention to provide an organ preservation system which incorporates a pump which can be used to perfuse organs in situ in the course of whole body perfusion done for removal of organs for transplantation or as a means to flush and reduce organ temperature in situ in a semi-invasive fashion until consent for organ donation is obtained.

In accordance with one form of the present invention, a homeostatic organ preservation system includes structure defining a chamber for holding a donor organ, and a pump for providing a perfusion solution to the organ. A first conduit is coupled to the pump and is adapted to be coupled to the organ. The first conduit provides perfusion solution from the pump to the organ. A second conduit is also coupled to the pump and to the structure defining the organ chamber. The second conduit is adapted to return perfusion solution from the organ chamber to the pump. The pump is operable to provide perfusion solution to the organ at a predetermined pump pulse pressure and pump stroke volume. Accordingly, the pump, first and second conduits and the organ chamber may be viewed as defining a circuit for recirculating perfusion solution between the organ and the pump.

The homeostatic organ preservation system further includes a pressure sensor which is coupled to the first conduit. The pressure sensor senses the pressure of the perfusion solution in the first conduit and provided to the organ. The pressure sensor provides an output signal which is indicative of the vascular resistance of the organ.

A pump control circuit is also provided. As its name implies, the pump control circuit controls the pump and is responsive to the output signal of the pressure sensor to raise and lower the pump pulse rate respectively in response to a decrease and increase in the organ vascular resistance.

In a more preferred form of the invention, the structure defining the organ chamber, pump and first and second conduits may all be housed in an outer insulated container, which container may be filled with crushed ice or the like to maintain the organ and the perfusate at a constant temperature whether the pump is on or off.

In accordance with one form of the method of perfusing a donor organ, an organ is placed in a chamber and connected to a first conduit which, in turn, is connected to a pump. The organ chamber is further connected to a second conduit which is also connected to the pump. The pump provides a perfusion solution to the organ through the first conduit, and the solution is returned to the pump via the second conduit.

The method further includes the step of monitoring the pressure of the perfusion solution in the first conduit. Since the pump stroke volume is constant, a change in pressure will be indicative of a change in the vascular resistance of the organ.

The method further includes the step of adjusting the pump pulse rate in accordance with the pressure of the perfusion solution in the first conduit, which pressure is indicative of the organ's vascular resistance. The pulse rate of the pump will be decreased if the pressure of the perfusion solution in the first conduit increases, which indicates that the vascular resistance of the organ has increased. The pump pulse rate will be automatically increased if the pressure of the perfusion solution in the first conduit decreases, indicating that the organ's vascular resistance has decreased.

Under normal physiologic conditions in the intact organism, active vasomotor control regulates tissue blood flow. In a state of hypothermia (such as is induced by cold perfusion), tissue denervation or tissue injury, this vasomotor mechanism is diminished or lost. In addition, vascular wall permeability may be altered, further compromising exchange between the intravascular space and the tissues. Conventional organ preservation machines try to mimic normal physiological conditions and ignore the particular requirements of hypothermic tissue. These machines provide too much flow at a high pulse rate which is damaging to the tissues. For proper hypothermic perfusion, the perfusion pressure should be sufficient to open all vessels and perfuse the tissues. Since protective vasomotor control is absent, a higher pressure than the minimal perfusion pressure can be damaging.

In the perfusion method of the present invention, this is accomplished by the present high threshold. However, if this pressure were maintained, then the continuous intravascular pressure would result in extravasation of fluids and result in edema. To minimize the possibility of edema and allow for flow from the tissue back into the intravascular space, the perfusion pressure is preferably pulsatile with a sufficient period of low pressure. The new perfusion method provides for a low pressure phase by means of the preset low pressure threshold.

Hypothermic tissue is also much more rigid. This requires a much slower pressure rise (dP/dT) than normal. The pressure rise dP/dT is optimal when the flow is in phase with the pressure. The rise in pressure can be adjusted independently from the high and low pressure thresholds by changing the flow rate of the pump at the beginning of a new pulse. This allows for synchronization of phase of pressure and flow. To complete the perfusion for hypothermic tissue, the proper stroke volume is preferably determined. The stroke volume is related to intravascular volume which is not changed by hypothermia. Therefore, the stroke volume may approximate the stroke volume under normothermic conditions for a given tissue. In the perfusion apparatus of the present invention, the stroke volume is regulated by the size or capacitance of a compliance chamber preferably used in the apparatus, as will be described in greater detail.

These and other objects, features and advantages of this invention will be apparent from the following detailed description of illustrative embodiments thereof, which is to be read in connection with the accompanying drawings.

DETAILED DESCRIPTION OF THE PREFERRED EMBODIMENTS

Figure 1:
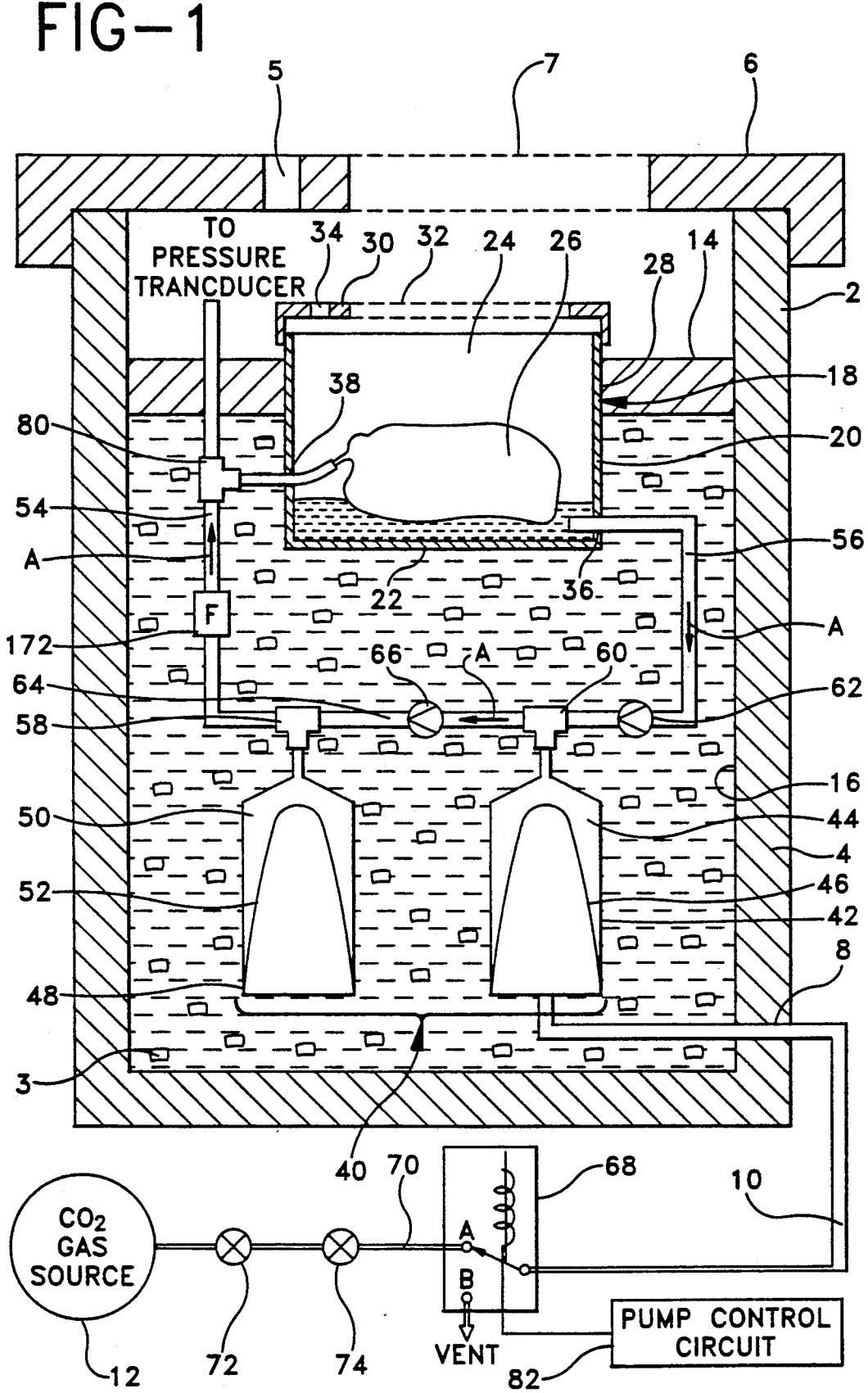
FIG. 1 is a pictorial illustration of one form of the apparatus of the present invention.

Referring initially to FIG. 1 of the drawings, it will be seen that an apparatus for perfusing a donor organ, constructed in accordance with the present invention, includes an outer container 2 which, as will be seen, is adapted to hold the organ and the other elements and components of the perfusion system. The outer container 2 includes insulated walls 4 formed of a highly insulative material, such as polystyrene or the like. Outer container 2 is made watertight so that it may be at least partially filled with crushed ice 3, in the event that the system is to be used for hypothermic organ perfusion.

Outer container 2 further includes an insulated top wall 14 which is preferably closely received between container walls 4, and is positioned across the upper portion of container 2. Thus, outer container 2 defines a leak-proof interior chamber 16 for receiving crushed ice. Insulated top wall 14 is removable so that container 2 may be filled with crushed ice 3.

The outer container 2 further includes a cover or lid 6 which couples snugly to the walls 4 of the container. The lid 6 includes a vent 5 or a gas permeable membrane 7 to allow room air to oxygenate the perfusion solution in the organ chamber, which will be described. However, lid 6 is water impermeable to prevent perfusion solution from leaking from container 2.

A gas input/output port 8 is formed through the thickness of container wall 4. Port 8 is adapted to receive a gas conduit 10 which, as will be seen, is adapted to be connected to a pump disposed internally of the container 2, as well as being coupled to a gas source 12. Of course, conduit 10 is closely received in port 8 so as to prevent ice and water from leaking from outer container 2.

The perfusion apparatus of the present invention further includes an interior container 18 disposed completely or at least partially within the interior of container 2. Interior container 18 includes side walls 20 and a bottom wall 22 connected to side walls 20. Side walls 20 and bottom wall 22 of container 18 thus define a chamber 24 for holding the donor organ 26.

Interior container 18 is closely received by an opening 28 formed in top wall 14 of container 2. Accordingly, top wall 14 supports container 18 so that container 18 extends into interior chamber 16 defined by container 2. In its preferred form, the walls 20 and 22 of container 18 are not insulated so that a organ 26 placed into chamber 24 will be further cooled by the crushed ice contained in interior chamber 16 of container 2.

Interior container 18 further includes a removable cover 30 which snugly mates with side walls 20. Cover 30 preferably includes a gas permeable membrane 32 which is provided so that the organ chamber 24 is exposed to room air to maintain oxygenation of the perfusate. However, membrane 32 is water impermeable so it will not leak. Cover 30 may further include a vent orifice 34 formed through its thickness. Vent 34 is provided for removing substantially all of the air from container 18.

Interior container 18 includes two openings 36, 38 which may be formed through side walls 20. As will be explained, each opening 36, 38 is formed to receive a conduit which provides perfusion solution to and removes perfusion solution from chamber 24.

The organ perfusion system of the present invention further includes a pump 40. Pump 40 generally includes a first container 42 which defines in its interior a perfusion solution drive chamber 44 and has mounted interiorly an elastic diaphragm 46. Similarly, pump 40 includes a second container 48 which defines a compliance chamber 50 and an elastic diaphragm 52 in its interior. Compliance chamber 50 is closed and, as will be described, mimics the aorta by acting as a capacitor to store energy in the form of gas pressure. Part No. 2118-008, which is a 250 ml. container manufactured by Nalgene Co., may be suitable for use as pump chambers 44, 50.

Pump 40, with its compliance chamber 50 and its drive chamber 44, is connected to the donor organ 26 and the organ chamber 24 by first and second conduits 54, 56, respectively. More specifically, compliance chamber 50 is in communication with organ 26 through the first conduit 54, with conduit 54 being connected to the main artery of organ 26, passing through opening 38 in interior container 18, with the other end of the conduit 54 being connected to a "T" fitting 58, whose second end is connected to second container 48.

Similarly, second conduit 56 is in communication with chamber 24 by having one of its ends pass through opening 36 in interior container 18. The other end of second conduit 56 is connected to a "T" fitting 60, whose second end is connected to first container 42.

In a preferred form of the invention, a one-way valve 62 may be positioned in line with second conduit 56 between "T" fitting 60 and interior container 18, with the valve situated such that it allows flow away from the interior container 18 toward drive chamber 44. The third ports of "T" fittings 58, 60 are connected together through a third conduit 64. In a preferred form, a one-way valve 66 may be positioned in line with third conduit 64, and situated such that flow of perfusion solution will be restricted to a direction toward compliance chamber 50 and away from drive chamber 44.

Pump 40 will cause perfusion solution to flow in the direction indicated by arrows A in FIG. 1. That is, the perfusion solution will flow into the main artery of the organ 26, and the venous effluent will be collected in interior container 18. The collected perfusion solution, after it has passed through organ 26, will be returned either by gravity or by a pump (not shown) through the second conduit 56 to drive chamber 44.

As mentioned previously, pump 40 is connected to a source of gas through conduit 10. More particularly, conduit 10 is connected to first container 42, defining drive chamber 44, and to a solenoid air valve 68.

Solenoid air valve 68 is positionable in two positions. In the first position of solenoid air valve 68, drive chamber 44 is in communication with gas source 12 through port A of solenoid air valve 68. In the second position of solenoid air valve 68, drive chamber 44 is in communication with the atmosphere, so that gas pressure in the first container 42 defining drive chamber 44 may be vented through port B of valve 68.

A source of gas 12, such as carbon dioxide in a pressurized cylinder, may be connected to port A of solenoid air valve 68 through a fourth conduit 70. Alternatively, and in a preferred form of the invention, a first gas regulator 72 is positioned in series with fourth conduit 70 to lower and regulate the air pressure from gas source 12. Preferably, first regulator 72 lowers the pressure in fourth conduit 70 to about 20 psi. A suitable regulator for use as regulator 72 is Part No. R83-200-RNEA, manufactured by Norgren Co.

A second regulator 74 may also be connected in series with fourth conduit 70 and positioned between first regulator 72 and port A of solenoid air valve 68. Second regulator 74 lowers the pressure in fourth conduit 70 to 2 psi. Part No. R38-200-RNEA, manufactured by Norgren Co., may be used for regulator 74. Accordingly, a gas pressure of 2 psi is provided to drive chamber 44 whenever solenoid air valve 68 is in a position to allow air flow through port A.

When solenoid air valve 68 is positioned to allow flow through port A, drive chamber 44 is pressurized, expelling solution from chamber 44 and causing perfusion solution to flow through first conduit 54 into the donor organ 26. This action also causes solution to flow into compliance chamber 50, compressing the gas on the other side of diaphragm 52.

When solenoid air valve 68 switches to allow air flow through port B, the pressurized gas in drive chamber 44 is vented to the atmosphere, causing perfusion solution collected in the bottom of interior chamber 18 to flow through second conduit 56 back to pump 40, for recirculation. More specifically, solution returned to the pump 40 by conduit 56 will fill drive chamber 44, expelling the gas from the other side of diaphragm 46. The pressure of the compressed gas in compliance chamber 48 will also force out the solution which has filled that chamber, which solution flows to organ 26. Compliance chamber 50 thus smoothes or integrates the pumping action of pump 40, in much the same way as the aorta smoothes the pumping action of the heart, to provide a more even flow.

The volume of the compliance chamber 48 is chosen so that it will at the minimum accommodate the stroke volume being used. Preferably, the volume of the compliance chamber is 5 to 10 times the stroke volume.

Figure 2:
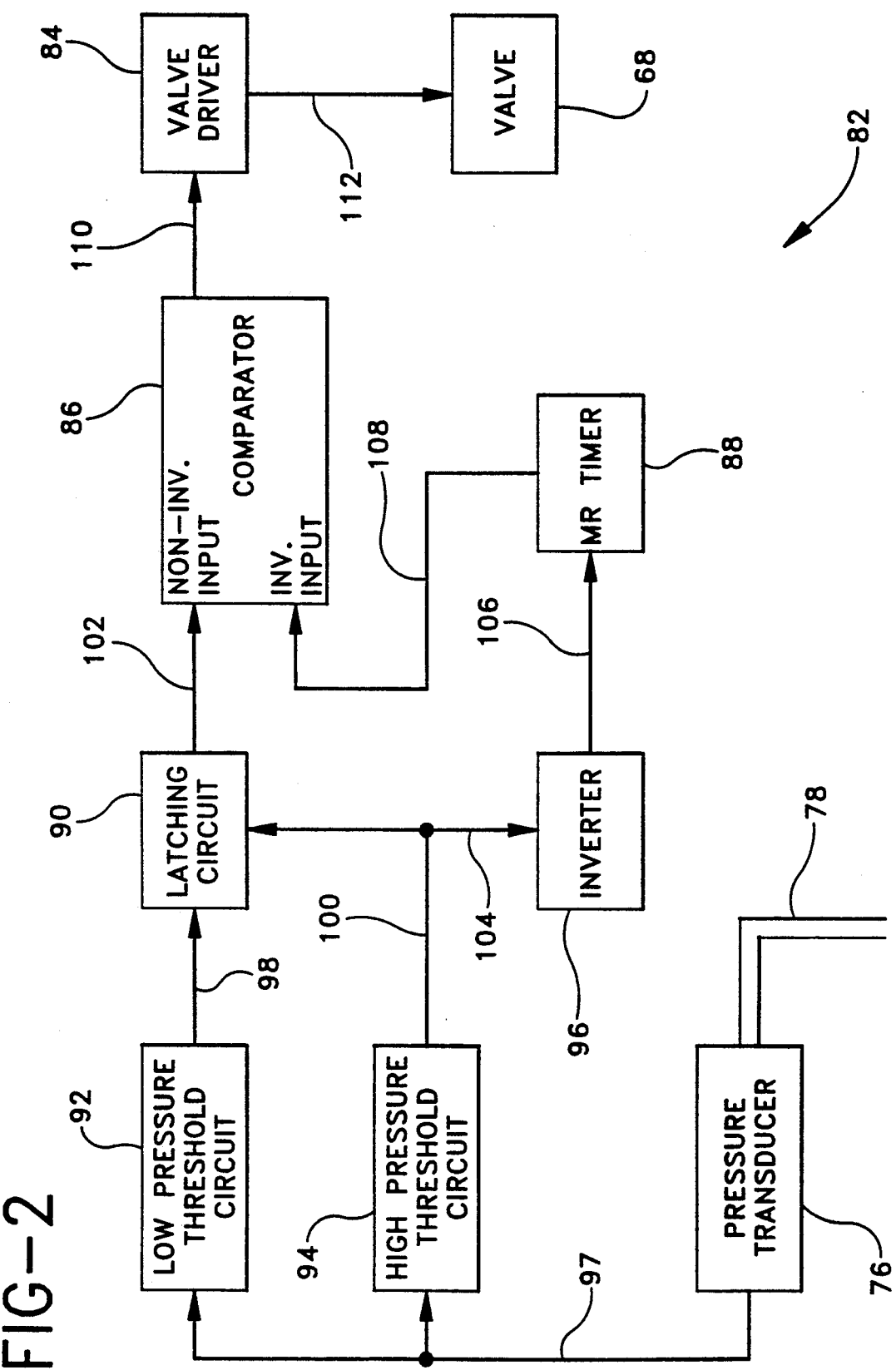
FIG. 2 is a block diagram of the pump control means illustrated by FIG. 1.
Figure 3:
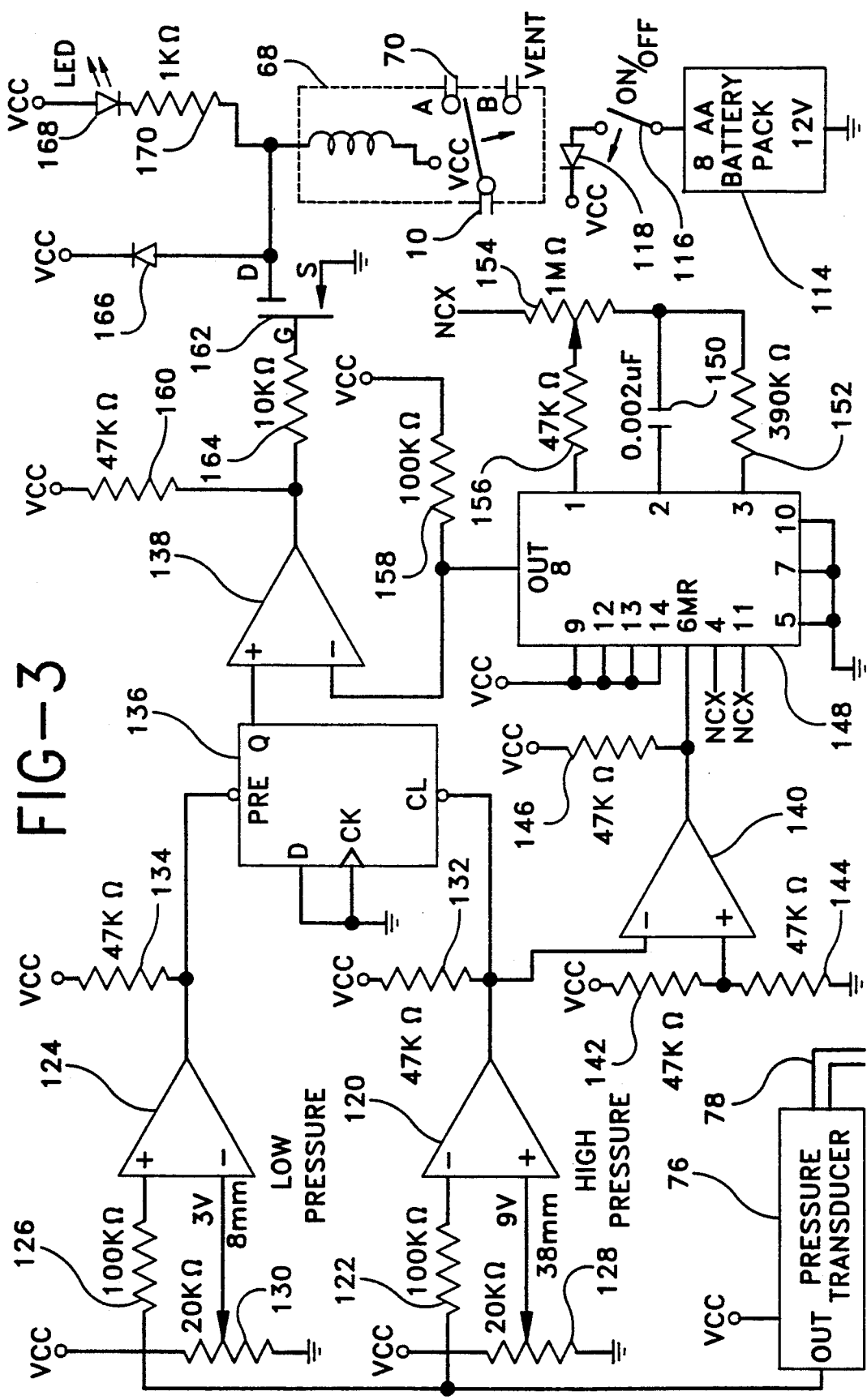
FIG. 3 is a schematic diagram of a preferred form of the pump control means illustrated by FIG. 2.

To measure the pressure of the perfusion solution flowing into the artery of organ 26, which pressure is indicative of the vascular resistance of the organ to the perfusion solution, a pressure transducer 76, as shown in FIGS. 2 and 3 of the drawings, is in communication with first conduit 54. More specifically, a fifth conduit 78 may be employed which is connected between pressure transducer 76 and a first port of a "T" fitting 80. The second and third ports of "T" fitting 80 are connected in series with first conduit 54 between compliance chamber 50 and organ 26. As will be explained, pressure transducer 76 is used to control the activation of solenoid air valve 68, which will control the pulse rate at which pump 40 supplies perfusion solution to organ 26.

The pressurized gas cylinder, solenoid air valve 68, pressure regulators 72, 74 and, as will be described, pump control circuit 82, may all be mounted on the outside wall or cover of container 2 while the pump and other components of the perfusion solution circuit are mounted inside container 2. Thus, the ice in container 2 will keep the organ as well as the perfusion solution cool, even if the solution is not circulating.

Referring now to FIG. 2 of the drawings, it will be seen that the homeostatic organ preservation system of the present invention further includes a pump control circuit 82.

Pump control circuit 82, which may be viewed as also including solenoid air valve 68, basically further includes a valve driver 84, a comparator circuit 86, a timer 88, a latching circuit 90, a low pressure threshold circuit 92 and a high pressure threshold circuit 94. An inverter 96 may also be included so that the timer 88 is activated on the inverse of the high threshold circuit's output signal. The operation of the pump control circuit 82 shown in FIG. 2 is described below.

Pressure transducer 76, which senses the pressure in first conduit 54 and, indirectly, the vascular resistance of the organ 26, produces an output signal which varies in amplitude in accordance with the pressure sensed in first conduit 54. This output signal is provided on signal line 97 to high threshold circuit 94 and low threshold circuit 92. If, for instance, the pressure in first conduit 54 is very low, that is, below the thresholds set by low threshold circuit 92 and high threshold circuit 94, low threshold circuit 92 will produce an output signal which is at a low logic level, and high threshold circuit 94 will produce an output signal which is at a high logic level. The output signals of low threshold circuit 92 and high threshold circuit 94 are provided respectively on signal lines 98 and 100 to latching circuit 90.

The output signal of latching circuit 90 is provided to the non-inverting input of comparator 86 on line 102. In response to the low logic level output signal from low threshold circuit 92 and the high logic level output signal from high threshold circuit 94, latching circuit 90 will provide an output signal which is at a high logic level to comparator 86.

High threshold circuit 94 also provides its output signal which, in the example given above, is at a high logic level, to inverter 96 on line 104. An output signal from inverter 96 is provided to the master reset (MR) input of timer 88 on line 106. Inverter 96 will thus invert the high logic level of the output signal of high threshold circuit 94 to a low logic level at the input of timer 88. Timer 88 is designed such that a positive logic level pulse on its input will cause timer 88 to reset internally and to generate an output signal in the form of a positive going pulse, which output signal is provided on line 108 to the inverting input of comparator 86.

Accordingly, in the example provided above, the output of timer 88 is at a low logic level, as it normally is, which output signal is provided to the inverting input of comparator 86 on line 108.

The output of comparator 86 is provided to the input of valve driver 84 on line 110. The output signal of comparator 86 is at a high logic level when the output of latching circuit 90 is at a high logic level and when the output signal of timer 88 is at a low logic level. A high logic level provided to the input of valve driver 84 on line 110 will turn on valve driver 84. Valve driver 84 controls valve 68 and is connected to valve 68 through line 112.

In the example given above, the output signal of pressure transducer 76 is relatively low, that is, it is at a voltage level which is lower than both a predetermined threshold voltage level set for the high threshold circuit 94 and a predetermined voltage threshold level which is set for low threshold circuit 92. As also explained previously, at such a voltage level from pressure transducer 76, valve driver 84 will turn on the solenoid air valve 68, enabling the pump 40 to operate and pump perfusion solution into organ 26.

As the pressure in first conduit 54 increases, pressure transducer 76 will detect this increase in pressure, and its output signal will accordingly increase in voltage. When the amplitude of the output signal of pressure transducer 76 rises above the predetermined threshold voltage level of low threshold circuit 92, the output of low threshold circuit 92 will change to a high logic level. However, the output signal on high threshold circuit 94 will remain at a high logic level, and latching circuit 90 will remain in its present state, with a high logic level as its output signal.

When the pressure in first conduit 54 detected by transducer 76 increases such that the amplitude of the output signal from transducer 76 rises above the predetermined voltage set with respect to the high threshold circuit 94, the output signal of the high threshold circuit 94 will change from a high logic level to a low logic level, which will cause the output signal of latching circuit 90 to change from a high logic level to a low logic level. The output signal of high threshold circuit 94 is also provided to inverter 96, and thus the signal provided to the input of timer 88 will change from a low logic level to a high logic level, resetting timer 88. When timer 88 is reset, its output signal will go to a high logic level.

The low logic level provided to the non-inverting input of comparator 86 by latching circuit 90 will cause the output signal of comparator 86 to go to a low logic level, causing valve driver 84 to turn solenoid valve 68 off. This, in turn, will cause the pump to stop pumping perfusion solution into the organ 26.

The pressure in first conduit 54 will decrease exponentially due to the vascular resistance of the organ and capacitance or storage effect of compliance chamber 50. The output signal from pressure transducer 76 will decrease in amplitude to below the predetermined voltage threshold level set with respect to high threshold circuit 94. The state of the output signal of high threshold circuit 94 will change from a low logic level to a high logic level. However, the output signal of latching circuit 90 will remain in its present low state.

The signal provided by inverter 96 to the input of timer 88 will now go to a low logic level. This will enable the timer to initiate a predetermined time delay. After the predetermined time delay has elapsed, the output of timer 88 will return to a low logic level. However, during the time that the output signal of timer 88 is at a high logic level, the output signal of comparator 86 will be kept at a low logic level, and valve driver 84 will continue to keep valve 68 in an off condition, disabling pump 40.

When the pressure of the perfusion solution in first conduit 54 drops to a level such that the output signal from transducer 76 falls in amplitude below the predetermined voltage threshold level of low threshold circuit 92, the output signal from threshold circuit 92 will change to a low logic level. Latching circuit 90, which receives the low logic level output signal from low threshold circuit 92, and the high logic level output signal from high threshold circuit 94, will change the state of its output signal from a low to a high logic level on line 102. If timer 88 has not timed out, that is, if the output signal of timer 88 is still at a high logic level, the output signal from comparator 86 will remain at a low logic level (as will be explained with respect to the embodiment illustrated by FIG. 3, a pull-up resistor, which is not shown in FIG. 2, may be used to ensure that the high logic level on signal line 108 is at least slightly higher than the high logic level on line 102, to prevent comparator 86 from changing the state of its output signal). Thus, valve driver 84 will continue to disable valve 68 and keep pump 40 in an off state.

However, when the output signal of timer 88 returns to a low logic level, comparator 86 will now provide a high logic level output signal. This will enable valve driver 84, which will turn valve 68 on and which, in turn, will cause pump 40 to start pumping perfusion solution to organ 26 again. The cycle of pump control circuit 82 stated above then repeats itself.

A chart illustrating the sequence of events in the cycle of the pump control circuit 82, as described previously, is shown below.

| Pressure in Conduit 54 mm Hg | Output Pressure Transducer Volt | Line #98 Low T. Logic | Line #100 High T. Logic | Line #106 M.R. Logic | Line #108 Timer Logic | Line #102 $Q_1$ Logic | Line #110 Driver Logic | Valve ON/OFF | Sequence | Description of Events |
|---|---|---|---|---|---|---|---|---|---|---|
| <8 | <3 | 0 | 1 | 0 | 1 | 1 | 0 | OFF | (1) | Power On, Pressure Low. Auto Reset Starts Time Delay. |
| <8 | <3 | 0 | 1 | 0 | 0 | 1 | 1 | ON | (2) | Time Delay Completed Pump Pressurized by Valve Turn On. |
| ≧8 | ≧3 | 1 | 1 | 0 | 0 | 1 | 1 | ON | (3) | Lower Threshold Reached. Pump Remains On. |
| 8–30 | 3–9 | 1 | 1 | 0 | 0 | 1 | 1 | ON | (4) | Flow Continues into Compliance Chamber and Organ, Pressure Rises. |
| ≧30 | ≧9 | 1 | 0 | 1 | 1 | 0 | 0 | OFF | (5) | Pressure Reached at Higher Threshold. Pump Turned Off. Timer Reset. |
| ≦30 | ≦9 | 1 | 1 | 0 | 1 | 0 | 0 | OFF | (6) | Pressure Drops Again. Blow High Threshold Time Delay Started. |
| 8–30 | 3–9 | 1 | 1 | 0 | 1 | 0 | 0 | OFF | (7) | Compliance Chamber Continues to Empty. |
| ≦8 | ≦3 | 0 | 1 | 0 | 1 | 1 | 0 | OFF | (8) | Low Threshold Reached. Timer Didn't Time Out Yet. |
| <8 | <3 | 0 | 1 | 0 | 0 | 1 | 1 | ON | (9) | Timer Timed Out. Cycle Restarts. |

The low pressure threshold is shown in the chart to be set at 3 volts, which corresponds to a pressure in conduit 54 of about 8 mm Hg. The high pressure threshold is also shown to be set at 9 volts, which corresponds to a pressure in conduit 54 of about 30 mm Hg. These are the preferred settings for the low and high pressure thresholds. The high and low pressure thresholds respectively correspond to the peak systolic pressure and the endiastolic pressure.

When the resistance to flow increases, more time will elapse before the pressure in conduit 54 declines to the lower pressure threshold. This will prolong the pulse period and therefore decrease the pulse rate. Vice versa, when the resistance to flow decreases, less time will elapse before the pressure in conduit 54 declines to the lower pressure threshold and the pulse rate will increase. The pulse rate can only increase up to the point where the pulse period becomes as short as the predetermined time delay.

The preset high pressure threshold protects the organ from too high a pulse pressure. The time delay or minimal pulse period and the low pressure threshold protect the organ from too much flow. This protection is desired because even high flow at low pressure may damage the organ's microvasculature.

By presetting the perfusion pressure thresholds and minimal pulse period, the optimum perfusion parameters can be chosen for every different temperature. By changing the size and/or pressure in the compliance chamber, the stroke volume can be adjusted to accommodate different sized organs.

The drawings of the pump chambers are schematic. In case a cell rich perfusate is used (i.e., blood), the pump chambers and the valves are made of highly biocompatible materials, such as polyurethane and/or silicone, while the contours and shape of the pump diaphragms and containers allow for non-turbulent flow and prevent stasis.

FIG. 3 shows a schematic diagram of a preferred form of the pump control circuit 82 shown in FIG. 2. The values of the components and part numbers of the integrated circuits described herein and shown in FIG. 3 are exemplary only and are understood not to limit the invention, as other values and components may be substituted for those shown by one skilled in the art.

Pump control circuit 82 is preferably powered by a battery 114, so that the entire system can be portable. Of course, it is envisioned to be within the scope of the invention to have other sources of AC or DC voltages power the unit. For purposes of illustration only, a 12-volt battery 114 comprised of 8 1.5 volt AA batteries connected in series is used. Battery 114 is connected to an on-off switch 116, which can be a single pole, single throw (SPST) switch. Switch 116 is then connected to a diode 118, whose anode is connected to the positive side of the battery through the switch. The cathode of diode 118 is then connected to the various components of the pump control circuit 82, the connection generally being shown by using the designation VCC. Diode 118 is used to protect the circuit in the event that the battery pack is inadvertently connected to the circuit in reverse polarity.

Pressure transducer 76 is preferably Model No. 142-SC-01D, manufactured by Sensym Manufacturing Corporation. Pressure transducer 76 produces an output signal which varies in voltage from approximately 0 volts to about VCC, which is approximately 12 volts, if pressure transducer 76 is powered by VCC. The output signal of pressure transducer 76 provided on the "output" terminal of pressure transducer 76 is provided to the inverting input of comparator 120 through a 100K ohm resistor 122, and to the non-inverting input of comparator 124 through a 100K ohm resistor 126. The non-inverting input of comparator 120 is connected to the wiper of a 20K ohm potentiometer 128, whose other terminals are connected to VCC and to ground. Similarly, the inverting input of comparator 124 is connected to the wiper of a 20K ohm potentiometer 130, whose other two terminals are connected to VCC and ground.

Comparator 120, and its associated resistors 122, 128, comprise the high threshold circuit 94 shown in FIG. 2. Similarly, comparator 124, and its associated resistors 126, 130, comprise the low threshold circuit 92 shown in FIG. 2. Potentiometer 128 is used to set the predetermined high threshold level of comparator 120, and potentiometer 130 is used to set the predetermined low threshold level of comparator 124.

Preferably, comparators 120, 124 comprise two comparators of quad-comparator integrated circuit LM339 or the like. Because the LM339 comparators have open collector outputs, a 47K ohm pull-up resistor 132 is connected between VCC and the output of comparator 120, and a similar 47K ohm resistor 134 is connected between VCC and the output of comparator 124.

The outputs of comparators 120 and 124 are respectively connected to the clear (CL) and preset (PRE) inputs of a D-type edge-triggered flip flop 136. Flip flop 136 is one-half of a dual D-type edge-triggered flip flop CMOS integrated circuit, such as part number MC7474 manufactured by Motorola Semiconductor Incorporated. Flip flop 136 is represented in FIG. 2 by latching circuit 90. The "D" and clock (CL) inputs of flip flop 136 are grounded, and the "Q" output of flip flop 136 is provided to the non-inverting input of a third comparator 138, which comparator is represented in FIG. 2 by comparator 86.

A fourth comparator 140 is used in the pump control circuit 82 shown in FIG. 3. The output of comparator 120 is provided not only to flip flop 136, but also to the inverting input of comparator 140. A voltage divider resistor network provides a predetermined voltage to the non-inverting input of comparator 140. The voltage divider resistor network includes a 47K ohm resistor 142 connected from VCC to the non-inverting input of comparator 140, and another 47K ohm resistor 144 connected between the non-inverting input of 140 and ground. Comparator 140 may be one of the comparators provided in the LM339 integrated circuit described previously. If such is the case, then a 47K ohm pull-up resistor 146 may be employed and connected between VCC and the output of comparator 140.

Comparator 140 inverts the output signal from comparator 120 and, as will be explained further, provides the inverted signal to the master reset (MR) input of programmable timer 148. Comparator 140 is represented in FIG. 2 by inverter 96.

Programmable timer 148 is preferably a CMOS logic integrated circuit, Part No. MC14541B, manufactured by Motorola Semiconductor Incorporated. Programmable timer 148 is represented in FIG. 2 by timer 88.

Programmable timer 148 will produce an output signal in the form of a high logic level pulse having a duration which is set externally to the integrated circuit by the selection of the values of certain capacitors and resistors connected to timer 148. If the above-described Part No. MC14541B is used for programmable timer 148, it is seen from FIG. 3 that pins 9, 12, 13 and 14 of the integrated circuit are connected to VCC, while pins 5, 7 and 10 are grounded. Pin 2 and pin 3 of programmable timer 148 are respectively connected to a 0.002 microfarad capacitor 150 and a 390K ohm resistor 152, whose other ends are connected together and to one end of a 1 megohm potentiometer 154. Pin 1 of programmable timer 148 is connected to one end of a 47K ohm resistor 156, whose other end is connected to the wiper of potentiometer 154. With the values of resistors 152 and 156 and capacitor 150 described above, the duration of a high level pulse provided on the output (pin 8) of programmable timer 148 will nominally be about 20 seconds, with adjustment provided by potentiometer 154. The output of timer 148 is provided to the inverting input of comparator 138. Preferably, a 100K ohm resistor 158 is connected to the output of timer 148 and to VCC to act as a pull-up resistor so that the signal from timer 148 is at least slightly higher than the signal from flip flop 136. This is to ensure that the output signal of comparator 138 does not go to a high logic level when both of its inputs are high.

As mentioned previously, comparator 138 is represented by comparator 86 in FIG. 2. It may also be one of he four comparators provided in integrated circuit Part No. LM339. If such is the case, a 47K ohm pull-up resistor 160 is provided and connected between VCC and the output of comparator 138.

Alternatively, comparator 86 may be replaced by a compatible 2-input logic gate which provides a high level output when the outputs of flip flop 136 and timer 148 (which are provided to the gate inputs) are high and low, respectively, and provides a low output at all other times.

The output of comparator 138 is connected to the gate of an N-channel MOSFET transistor 162 through a 10K ohm gate resistor 164. The source of transistor 162 is connected to ground, while the drain of transistor 162 is connected to VCC through diode 166. More specifically, the anode of diode 166 is connected to the drain of transistor 162, while the cathode of diode 166 is connected to VCC. Diode 166 is provided for spike protection, as will be described.

Transistor 162 may be Part No. IRFD220 manufactured by International Rectifier Corp. in El Segundo, Calif. Transistor 162 is represented as the valve driver 84 in FIG. 2.

The drain of transistor 162 is connected to one end of the solenoid or coil of valve 68, and the other end of the solenoid is connected to VCC. When the solenoid de-energizes, diode 166 may conduct to VCC if any over-voltage transients are produced, in order to protect transistor 162. Solenoid air valve 68 is preferably a three-way air valve, Part No. 3E1/12V, manufactured by Humphrey Manufacturing Company.

A light-emitting diode (LED) 168 is also provided. Light-emitting diode is connected with its anode to VCC and its cathode to the drain of transistor 162 through a 1K ohm resistor 170 LED 168 will conduct and light whenever the solenoid is energized to turn pump 40 on.

The pump control circuit 82 shown schematically in FIG. 3 works in the same manner as described with respect to the block diagram of the circuit shown in FIG. 2. Potentiometer 130, which adjusts the low pressure threshold level, is set to provide approximately 3 volts at the inverting input of comparator 124, which corresponds to a pressure of 8 millimeters of mercury. Potentiometer 128, which adjusts the high level pressure threshold, is set to provide 9 volts at non-inverting input of comparator 120, which corresponds to a pressure of about 30 millimeters of mercury.

Assuming initially that pressure transducer 76 produces an output voltage level which is below both the high and low threshold levels set by potentiometer 128 and 130, the outputs of comparators 120 and 124 will be respectively at high and low logic levels. Accordingly, a low logic level is provided by comparator 124 to the preset of flip flop 136, causing the "Q" output of flip flop 136 to go to a high logic level.

Timer 148 includes an auto-reset feature. Upon initial power turn on, the auto-reset of timer 148 will be activated and provide a logic high output for the duration of the predetermined time delay.

If the inverting input of comparator 138 is high, the output of comparator 138 will be at a logic low. After the timer has timed out, the inverting input of comparator 138 will go to a low logic level. This will change the output of comparator 138 to a high logic level since the non-inverting input remains high. This will bias transistor 162 so that it is on and conducting current through the solenoid of valve 68. The switch contacts of valve 68 will be in the "A" position, as shown in FIG. 2, to allow gas from source 12 to flow into drive chamber 44 of pump 40, causing perfusion solution to flow through first conduit 54 into organ 26.

As the pressure in conduit 54 increases, pressure transducer 76 will detect this increase and provide an output signal of greater voltage. As the output signal of transducer 76 increases, it will rise above the 3 volt threshold level set by potentiometer 130, causing comparator 124 to switch to a high logic level on its output. However, the high logic level provided to the preset of flip flop 136 will not affect the logic level on the "Q" output of the flip flop. Accordingly, pump 40 remains on.

As the pressure in first conduit 54 increases further, the output voltage of transducer 76 will reach the high threshold level set by potentiometer 128, that is, 9 volts. At this point, comparator 120 will switch from a high to a low logic level on its output. The low logic level is provided to the clear (CL) input of flip flop 136, causing the "Q" output of flip flop 136 to switch from a high logic level to a low logic level. This transition on the output of comparator 120 is inverted by comparator 140 so that the master reset input of programmable timer 148 is provided with a high logic level. The transition from low to high will reset timer 148, and the output of timer 148 will go to a high logic level.

The low logic level provided on the non-inverting input of comparator 138, or the high logic level provided by the timer 148 on the inverting input of comparator 138, will cause the output of the comparator to go to a low logic level, cutting off transistor 162, i.e., so that it no longer conducts current through the solenoid of valve 68. The associated switch of valve 68 will switch to the "B" position (see FIGS. 1 and 3) so that the gas in drive chamber 44 will be vented to the atmosphere. Pump 40 will stop circulating perfusion solution to the organ and the pressure in conduit 54 will drop.

As the pressure drops, the amplitude of the output signal of transducer 76 will decrease below the value set for the high pressure threshold by potentiometer 128. Such will cause the output of comparator 120 to return to a high logic level, but this will not affect the state of flip flop 136.

The master reset input of timer 148 will, however, go to a low logic level and, accordingly, the master reset input of timer 148 to a low logic level. This high-to-low transition on the master reset input of timer 148 will trigger the timer. The output signal from timer 148 will remain at a high logic level for a predetermined duration, which is nominally set for 20 seconds from the time it is triggered. Thus, transistor 162 will remain in the cut-off condition, and solenoid valve 68 will remain de-energized.

When the pressure in conduit 54 has decreased to such a point that the output voltage of transducer 76 has fallen below the lower threshold set by potentiometer 130, the output of comparator 124 will go to a low logic level, causing the "Q" output of flip flop 136 to change to a high logic level. This will cause the output of comparator 138 to return to a high logic level, but only if programmable timer 148 has timed-out (that is, only if the output signal on timer 148 has returned to a low logic level). When the output of comparator 138 returns to a high logic level, it will turn transistor 172 on so that current is conducted through the solenoid of valve 68, switching the solenoid back to position "A" to allow gas to enter drive chamber 44, causing pump 40 to pump perfusion solution into organ 26.

Note that every time transistor 162 is turned on to conduct current through the solenoid of valve 68, current is also conducted through LED 168, which lights to indicate that the pump 40 is pumping perfusion solution into organ 26.

The above-described cycle will repeat itself periodically.

Figure 4:
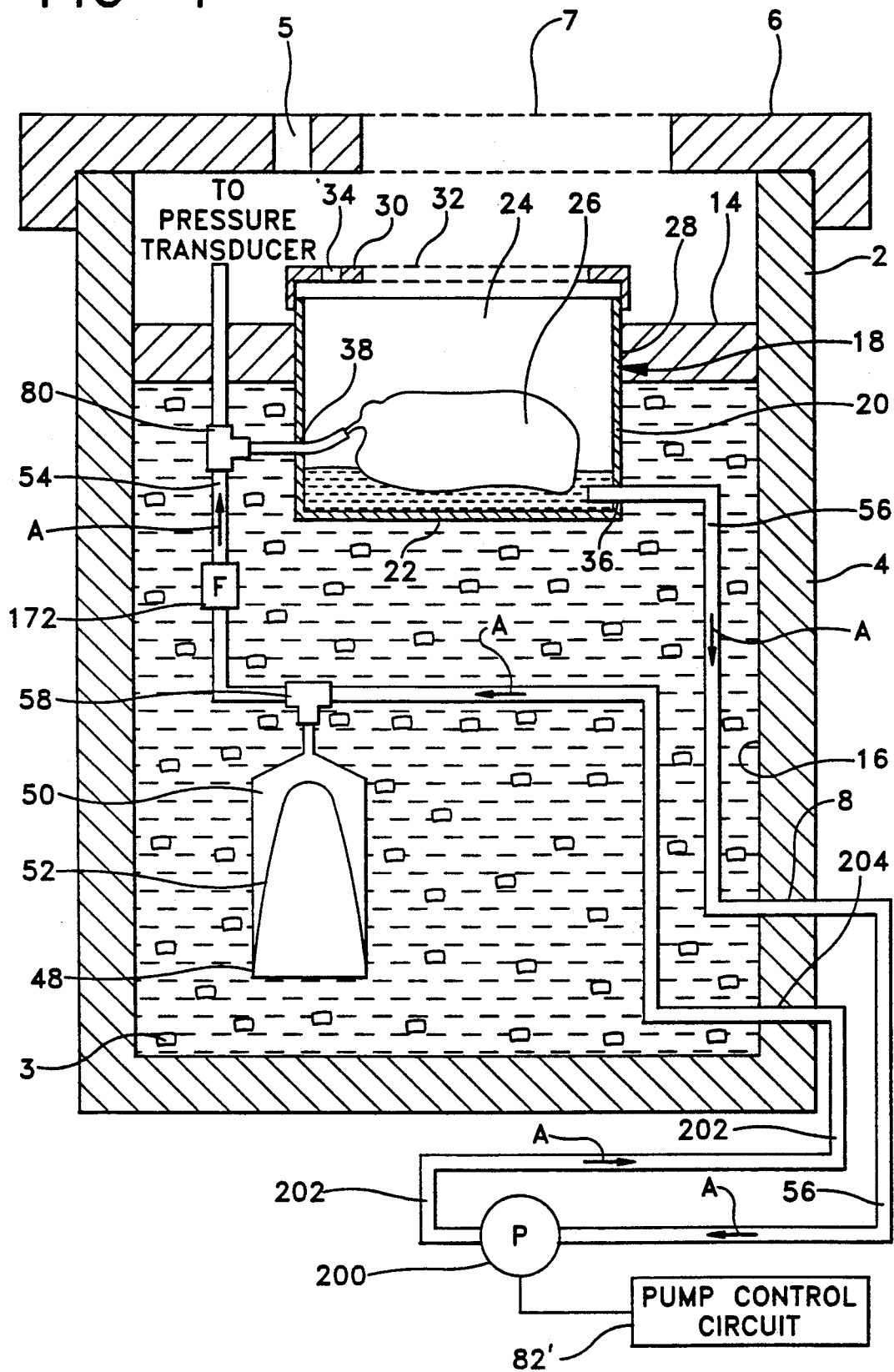
FIG. 4 is a pictorial illustration of a second form of the apparatus of the present invention.
Figure 5:
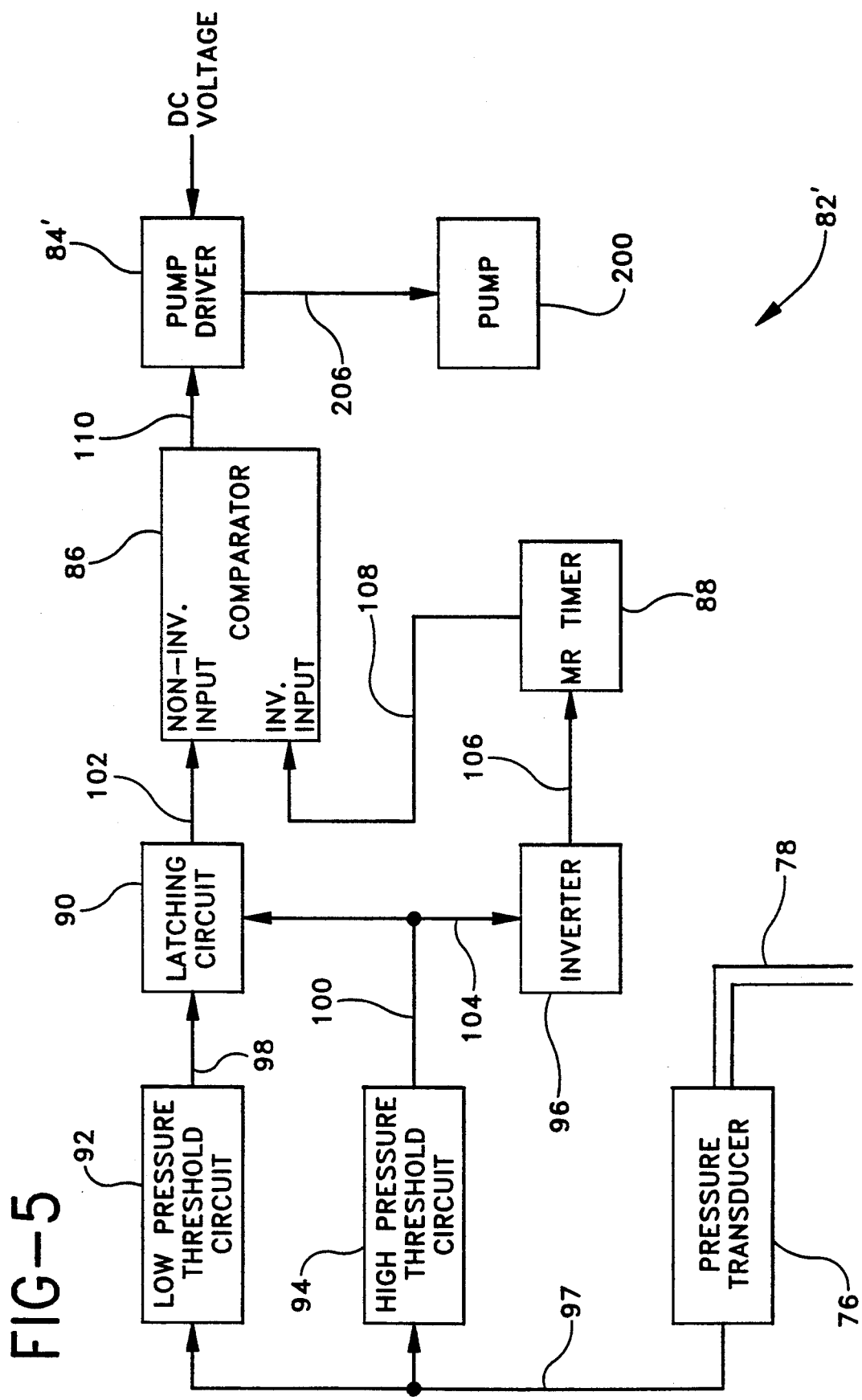
FIG. 5 is a block diagram of the pump control means illustrated by FIG. 4.
Figure 6:
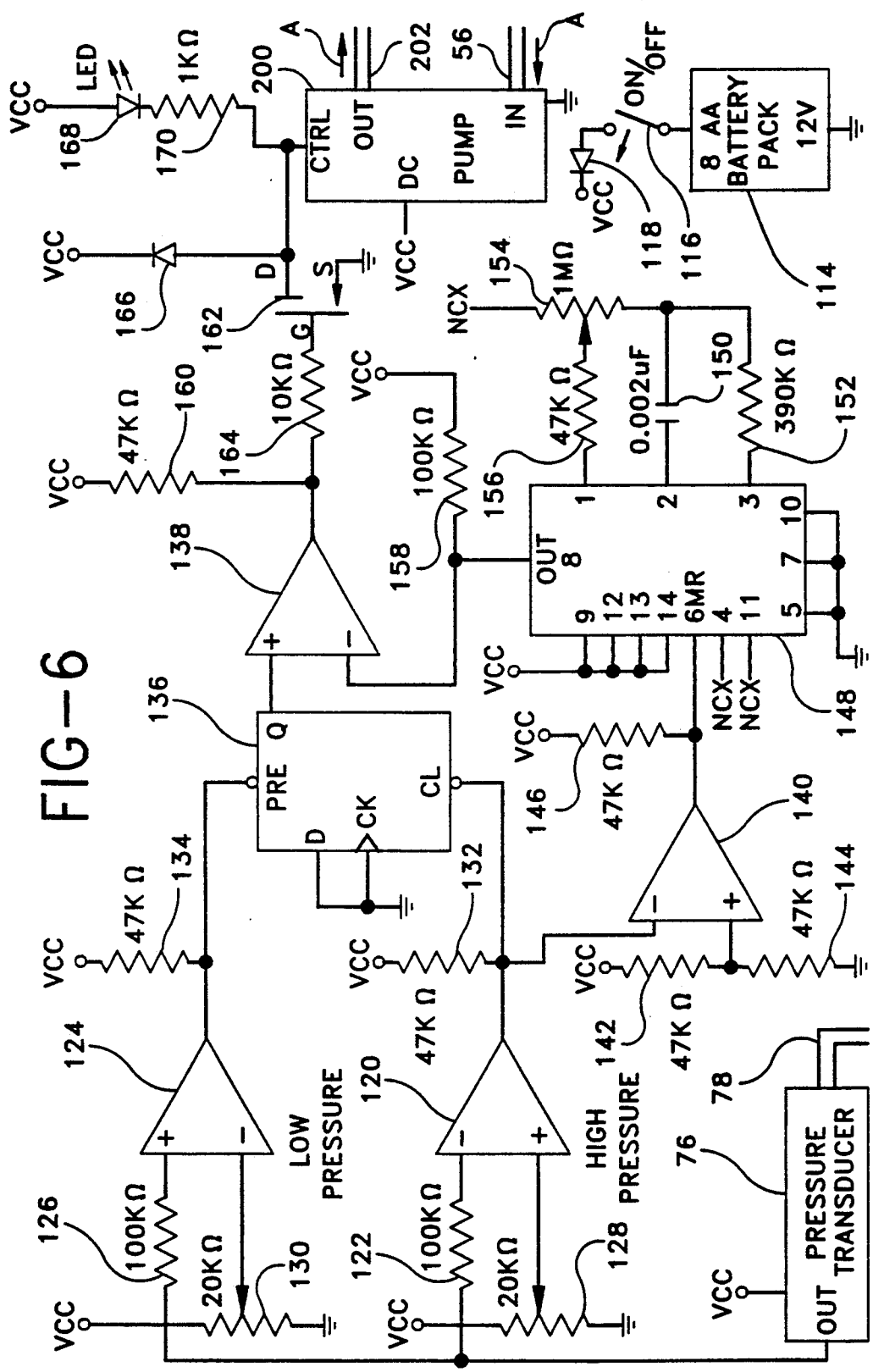
FIG. 6 is a schematic diagram of a preferred form of the pump control means illustrated by FIG. 5.

An alternative form of the homeostatic organ preservation system of the present invention is illustrated by FIGS. 4–6. The alternative form of the system is similar in structure, circuitry and function to the system shown in FIGS. 1–3 and described previously, and like reference numerals are used to indicate similar components.

Referring initially to FIG. 4 of the drawings, it will be seen that the alternative form of the organ preservation system comprises most of the basic components of the first form shown in FIG. 1, and preferably includes the insulated outer container 2, the cover 6, interior organ container 18, perfusion flow conduits 54 and 56, and all of the other components of the first system connected in the manner described previously, except that one-way valves 62, 66, conduit 64, first pump container 42 defining drive chamber 44, fitting 60, and gas conduit 10 are preferably omitted. In addition, the $CO_2$ gas source 12, regulators 72, 74, conduit 70 and solenoid valve 68 are preferably eliminated from this embodiment of the system.

In accordance with the second form of the invention, the second or return conduit 56 passes through port 8 of container 4 and is coupled to the input port of a separate pump 200, which may be mounted on the exterior surface of container 4. Pump 200 replaces, in effect, first container 42 defining drive chamber 44, and eliminates the need for a source of compressed gas.

Several types of pumps may be utilized as pump 200, many of which are commercially available, as long as certain specifications are preferably met. It is preferred if pump 200 has an adjustable flow rate, allows for intermittent operation to provide pulsatile flow, and is small enough to be portable with the rest of the system. In addition, the pump preferably should not contaminate the perfusate and should be safe for protein and cell containing solutions. Possible pump types which may be used as pump 200 include a roller pump, a bellows or diaphragm operated pump, an impeller pump, a piston pump, a pusher plate pump or any other pump which preferably meets the above specifications. A suitable roller pump 200 which may be used as pump 200 is Part No. SK10 manufactured by Sarnes Inc. located in Ann Arbor, Mich.

The output port of pump 200 is connected to a conduit 202 which passes through a second port 204 formed through the thickness of insulated container 4. Conduit 202 is connected to fitting 58 so that roller pump 200 is coupled to second container 48 defining the compliance chamber 50. A pump control input terminal on pump 200 is connected to a pump control circuit 82', which is similar in many respects to pump control circuit 82 and which will be described in greater detail.

As in the previous embodiment, container 4 is made from a temperature insulating material. Hypothermia of the organ chamber 24 and perfusion circuit is maintained by melting ice or other cooling means. The pump control circuit 82', the pump 200 and the power supply may be attached to the outside of the container 4 or placed in a separate liquidproof chamber within container 4, if for example pump 200 is not submersible in the cooling medium. Alternatively, pump 200 may be situated inside container 4 in a manner similar to drive chamber container 42. By mounting pump 200 inside the container, there is no need for conduits 56 and 202 to pass through the container wall and be exposed to ambient temperatures. Thus, the entire perfusion circuit will be exposed to the cooling medium inside the container 4.

The homeostatic organ preservation system illustrated by FIG. 4 operates in a manner similar to that shown in FIG. 1. Pump 200 receives perfusion solution returned to it from organ chamber 24, and pumps solution through first conduit 54 into the donor organ 26. This action also causes solution to flow into compliance chamber 50, which is effectively placed in series with pump 200 and the perfused organ, compressing the gas on the other side of diaphragm 52, as it did in the embodiment of FIG. 1. The pressure of the compressed gas in compliance chamber 50 will also force out the solution which has filled that chamber, which solution flows to organ 26. As mentioned previously in regard to the embodiment shown in FIG. 1, compliance chamber 50 of this alternative embodiment smoothes or integrates the pumping action of the pump to provide a more even flow. The capacity of the compliance chamber 50 is selected to provide a certain stroke volume. The capacity of the compliance chamber and adjustments in the flow rate of the pump 200 allow for the synchronization of the phase of the flow to the phase of the pressure.

The pump control circuit 82' is generally similar in structure and function to control circuit 82 of the first embodiment. As shown in block diagram form in FIG. 5, pump control circuit 82' includes low and high pressure threshold circuits 92, 94, which effectively compare the perfusion pressure with preset low and high thresholds, pressure transducer 76 which measures the perfusion pressure, latching circuit 90, inverter 96, timer 88 which limits the maximum pulse rate, and comparator 86, which is used for starting and stopping the action of the pump. Each of these components is included in the preferred form of the embodiment shown in FIG. 2, and all of these components in the second form of the system are interconnected in the manner described previously in relation to the embodiment of FIG. 2.

The pump control circuit 82' includes a pump driver 84' coupled to comparator 86 by line 110 and to pump 200 by line 206. Pump driver 84' functions in a manner similar to valve driver 84 described previously to drive pump 200 in response to the output signal comparator 86.

FIG. 6 shows a schematic diagram of a preferred form of the pump control circuit 82' shown in FIG. 5. The components of the pump control circuit 82' are basically the same as those of circuit 82 shown in FIG. 3, and these components are interconnected in the same manner described previously, except that solenoid valve 68 is omitted, and the drain of transistor 162 and one end of resistor 170 are coupled directly to the pump control input terminal (CTRL) of pump 200. In addition, a DC voltage VCC is provided directly to the DC input of pump 200. Pump circuit 82' functions generally in the same manner in controlling pump 200 as circuit 82 functions in controlling solenoid valve 68.

It is evident from the above description of the homeostatic organ preservation system that the system automatically responds to changes in vascular resistance by altering the pulse rate of the pump while the systolic perfusion pressure and the stroke volume remain constant. The differential of pressure over time (dP/dt) may be adjusted independently from stroke volume and pulse pressure to match the decreased compliance of the hypothermic organ, or body if perfusion of the whole body is being performed. The appropriate settings of potentiometers 128, 130, which control the high and low pressure thresholds, and of potentiometer 154, which controls the duration of timer 148, for a particular type of organ can be precalibrated at the time of manufacturing the system, after which no further adjustments by the user are necessary. Also, if the system is to be used for normothermic perfusion, the normal physiologic flow parameters may be set.

The timer circuit is advantageous in that it will prevent the pump from operating at too fast a rate. This will minimize any damage to the organ's microvasculature which may result from a high flow rate of perfusate even at a low pressure. In other words, the system of the present invention guarantees that peak pressure is provided to the organ to perfuse all of its vessels, and provides a high flow rate but not a damaging flow. The 1 megohm potentiometer 154 will provide an adjustment to the pump pulse rate of from about 6 beats per minute to about 0.5 beats per minute. Potentiometer 154 is adjusted in accordance with the temperature at which the organ is being perfused.

The entire perfusion system (i.e., the pump, organ chamber and interconnecting conduits) is contained in one insulated container 2; therefore, the organ and the perfusate are maintained at a constant temperature whether the pump is on or off. The constant temperature maintained in the system allows for exact redox control of the perfusate.

For a perfusion at different temperatures, it is envisioned that a temperature sensor (not shown) be employed which can automatically correct the perfusion parameters (i.e., the high and low threshold levels and the timer duration) as required.

Also, it is envisioned to incorporate a perfusate filter 172 (see FIG. 1) in the system, preferably in line with first conduit 54, having a 0.2 micrometer pore size to prevent damage by cryoprecipitants or to clear the perfusate of cellular components. The advantage of the system described above is that the pump will automatically adjust to any pressure drop that might occur due to the filter. A 0.2 μm bypass filter, Part No. PP3802 manufactured by Pall Corporation, is suitable for use as filter 172.

All of the components of the system of the present invention are highly biocompatible, and the perfusate is not exposed to high shear forces during perfusion. These features reduce the denaturization of proteins and minimize the hemolysis of cells in the perfusate.

The internal power supply 114 is sufficient for several days of independent operation. This is also attributable to the low current drain resulting from the use of CMOS logic.

The entire unit is portable and weighs approximately six kilograms, and, in its preferred form, is relatively small with the dimensions of 38 centimeters in height by 27 centimeters in width by 21 centimeters in depth. It is quite smaller and lighter than current machines which weigh more than 25 kilograms and are three times larger.

Also, the system of the present invention is quite inexpensive to manufacture and use. The approximate cost of the materials are $125.00 in reusable components and $50.00 in disposable materials. The simple construction requires approximately three man-hours for assembly.

The method and apparatus of the present invention provide the optional perfusion for tissues which have an altered or absent vasomotor regulation, as occurs during hypothermia, and is therefore ideal for organ preservation for the purpose of transplantation. As is evident from the previous description, the perfusion method of the present invention meets four basic design objectives: 1) the perfusion of the organ is pulsatile wherein a new pulse starts substantially at the time the pressure returns to a preset level; 2) the pulse pressures may be preset and are substantially unaffected by changes in the vascular resistance of the tissue; 3) the stroke volume is substantially constant and substantially equals the stroke volume under normal physiological conditions for a given perfused organ; and 4) the phase of flow is substantially synchronous with the phase of pressure. In addition, for a given application, as for example human kidney preservation, the perfusion pressure threshold levels and the volume of the compliance chamber may be standardized.

The homeostatic organ preservation system of the present invention is more adaptable than conventional perfusion devices to further improvements. For example, filters, gas exchangers and redox controllers may easily be placed in series with the apparatus of the present invention without substantially affecting perfusion characteristics.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A homeostatic organ preservation system, which comprises:
   means defining a chamber for holding a donor organ;
   a pump for providing a perfusion solution to the organ, the pump being operable to provide perfusion solution to the organ at a predetermined pump pulse pressure and a predetermined pump stroke volume;
   a first conduit coupled to the pump and adapted to be coupled to the organ, the first conduit being adapted to provide perfusion solution from the pump to the organ;

a second conduit coupled to the pump and communicating with the organ chamber, the second conduit being adapted to return perfusion solution from the organ chamber to the pump;

a pressure sensor coupled to the first conduit to sense the pressure of the perfusion solution in the first conduit and provided to the organ, the pressure sensor providing an output signal being indicative of the vascular resistance of the organ; and pump control means for controlling the pump, the pump control means being responsive to the output signal of the pressure sensor to raise and lower the pump pulse rate respectively in response to a decrease and increase in the organ vascular resistance.

2. A system as defined by claim 1, wherein the pump control means includes first and second pressure threshold comparators, the first pressure threshold comparator being responsive to the output signal of the pressure sensor and providing an output signal indicative of the relative amplitude of the output signal of the pressure sensor with respect to a first predetermined threshold value, the second pressure threshold comparator being responsive to the output signal of the pressure sensor and providing an output signal indicative of the relative amplitude of the output signal of the pressure sensor with respect to a second predetermined pressure value.

3. A system as defined by claim 2, wherein the pump control means further includes latching means, the latching means being responsive to the output signals of the first and second pressure threshold comparators and providing an output signal in response thereto.

4. A system as defined by claim 3, wherein the pump control means further includes timer means, the timer means being responsive to the output signal of the second pressure threshold comparator and providing an output signal in the form of a pulse of a predetermined duration.

5. A system as defined by claim 4, wherein the pump control means further includes a third comparator, the third comparator being responsive to the output signal of the latching means and the output signal of the timer means and providing an output signal in response thereto.

6. A system as defined by claim 5, wherein the pump control means further includes valve driver means, the valve driver means being responsive to the output signal of the third comparator and providing an output signal in response thereto.

7. A system as defined by claim 6, wherein the pump control means further includes a gas valve, the gas valve being responsive to the output signal of the valve driver means to selectively provide pressurized gas to the pump in response thereto.

8. A system as defined by claim 5, wherein the pump control means further includes pump driver means, the pump driver means being responsive to the output signal of the third comparator and providing an output signal in response thereto, the pump being responsive to the output signal of the pump driver means to provide perfusion solution to the organ.

9. A homeostatic organ preservation system, which comprises:

an outer container, the outer container having side walls formed of a thermally insulating material, the outer container being substantially liquid-tight and defining a first chamber in the interior thereof;

an inner container, the inner container being at least partially disposed within the first chamber of the outer container, the inner container defining a second chamber for receiving an organ;

a cover removably mounted on at least one of the inner container and the outer container, the cover including means for allowing air to pass therethrough;

a pump for providing a perfusion solution to an organ disposed in the second chamber, the pump being disposed within the first chamber of the outer container;

at least a first and second conduit for respectively supplying perfusion solution to the organ and removing solution from the second chamber, the first and second conduits being disposed in the first chamber, the first conduit providing communication between the organ and the pump, and the second conduit providing communication between the second chamber and the pump;

a pressure sensor coupled to the first conduit to sense the pressure of the perfusion solution in the first conduit and provided to the organ, the pressure sensor providing an output signal being indicative of the vascular resistance of the organ; and pump control means for controlling the pump, the pump control means being responsive to the output signal of the pressure sensor to raise and lower the pump pulse rate respectively in response to a decrease and increase in the organ vascular resistance;

wherein the pump, first and second conduits and second chamber define a circuit for recirculating perfusion solution between the organ and the pump, the circuit being contained within the first chamber.

10. A system as defined by claim 9, wherein the pump includes means defining a pump chamber and means defining a compliance chamber, the pump chamber and compliance chamber being in communication with one another and with the perfusion solution circuit defined by the first and second conduits and the second chamber.

11. A system as defined by claim 10, wherein the second conduit is connected between the second chamber and the pump chamber, and the first conduit is connected to the compliance chamber and is in communication with the organ.

12. A system as defined by claim 11, which further includes a first one-way valve coupled to the second conduit to allow flow of perfusion solution in a direction only from the second chamber to the pump chamber, and a second one-way valve operatively disposed between the pump chamber and the compliance chamber to allow flow of perfusion solution in a direction only from the pump chamber to the compliance chamber.

13. A system as defined by claim 9, which further includes a filter disposed in series communication with the perfusion solution circuit defined by the pump, first and second conduits and the second chamber.

14. A homeostatic organ preservation system, which comprises:

means defining a chamber for holding a donor organ;

a pump for providing a perfusion solution to the organ, the pump being operable to provide perfusion solution to the organ at a predetermined pump pulse pressure and a predetermined pump stroke volume;

a first conduit coupled to the pump and adapted to be coupled to the organ, the first conduit being adapted to provide perfusion solution from the pump to the organ;

a second conduit coupled to the pump and communicating with the organ chamber, the second conduit being adapted to return perfusion solution from the organ chamber to the pump;

a pressure sensor coupled to the first conduit to sense the pressure of the perfusion solution in the first conduit and provided to the organ, the pressure sensor providing an output signal being indicative of the vascular resistance of the organ;

a pump control circuit, the pump control circuit including:

a first comparator, the first comparator being provided with a low pressure threshold voltage and being responsive to the output signal of the pressure sensor, the first comparator providing an output signal indicative of the relative amplitude of the output signal of the pressure sensor with respect to the low pressure threshold voltage;

a second comparator, the second comparator being provided with a high pressure threshold voltage and being responsive to the output signal of the pressure sensor, the second comparator providing an output signal indicative of the relative amplitude of the output signal of the pressure sensor with respect to the high pressure threshold voltage;

a latching circuit, the latching circuit being responsive to the output signals of the first and second comparators and providing an output signal in response thereto;

a timer, the timer being responsive to the output signal of the second comparator and being triggered thereby when the amplitude of the output signal of the pressure sensor decreases from above to below the high pressure threshold voltage, the timer providing an output signal in the form of a pulse of a predetermined duration;

means responsive to the output signals of the latching circuit and the timer and providing an output signal in response thereto;

valve driver means, the valve driver means being responsive to the output signal of the timer an latching circuit responsive means and providing an output signal in response thereto; and a gas valve, the gas valve being responsive to the output signal of the valve driver means to selectively provide pressurized gas to the pump in response thereto.

15. A homeostatic organ preservation system, which comprises:

means defining a chamber for holding a donor organ;

a pump for providing a perfusion solution to the organ, the pump being operable to provide perfusion solution to the organ at a predetermined pump pulse pressure and a predetermined pump stroke volume;

a first conduit coupled to the pump and adapted to be coupled to the organ, the first conduit being adapted to provide perfusion solution from the pump to the organ;

a second conduit coupled to the pump and communicating with the organ chamber, the second circuit being adapted to return perfusion solution from the organ chamber to the pump;

a pressure sensor coupled to the first conduit to sense the pressure of the perfusion solution in the first conduit and provided to the organ, the pressure sensor providing an output signal being indicative of the vascular resistance of the organ;

a pump control circuit, the pump control circuit including:

a first comparator, the first comparator being provided with a low pressure threshold voltage and being responsive to the output signal of the pressure sensor, the first comparator providing an output signal indicative of the relative amplitude of the output signal of the pressure sensor with respect to the low pressure threshold voltage;

a second comparator, the second comparator being provided with a high pressure threshold voltage and being responsive to the output signal of the pressure sensor, the second comparator providing an output signal indicative of the relative amplitude of the output signal of the pressure sensor with respect to the high pressure threshold voltage;

a latching circuit, the latching circuit being responsive to the output signals of the first and second comparators and providing an output signal in response thereto;

a timer, the timer being responsive to the output signal of the second comparator and being triggered thereby when the amplitude of the output signal of the pressure sensor decreases from above to below the high pressure threshold voltage, the timer providing an output signal in the form of a pulse of a predetermined duration;

means responsive to the output signals of the latching circuit and the timer and providing an output signal in response thereto; and pump driver means, the pump driver means being responsive to the output signal of the timer and latching circuit responsive means and providing an output signal in response thereto, the pump being responsive to the output signal of the pump driver means to provide perfusion solution to the organ.

16. A method of perfusing an organ, the organ being placed in a chamber and connected to a first conduit which is connected to a pump, the chamber being in communication with the pump through a second conduit, the pump providing a perfusion solution to the organ through the first conduit and the solution being returned to the pump through the second conduit, the pump being operable to provide perfusion solution to the organ at a predetermined pump pulse pressure and predetermined pump stroke volume, the method comprising the steps of:

monitoring the pressure of the perfusion solution in the first conduit, the pressure being indicative of the vascular resistance of the organ being perfused; and adjusting the pump pulse rate in accordance with the pressure of the perfusion solution in the first conduit, the pulse rate of the pump being decreased if the pressure of the perfusion solution in the first conduit increases, and being increased if the pressure of the perfusion solution in the first conduit decreases.

17. A method of perfusing an organ, the organ being placed in a chamber and connected to a first conduit which is connected to a pump, the chamber being in communication with the pump through a second conduit, the pump providing a perfusion solution to the organ through the first conduit and the solution being returned to the pump through the second conduit, the method comprising the steps of:

monitoring the pressure of the perfusion solution in the first conduit, the pressure being indicative of the vascular resistance of the organ being perfused;

comparing a low pressure threshold with the monitored pressure of the perfusion solution and providing a first signal indicative of the relative magnitude of the monitored pressure with respect to the low pressure threshold;

comparing a high pressure threshold with the monitored pressure of the perfusion solution and providing a second signal indicative of the relative magnitude of the monitored pressure of the perfusion solution with respect to the high pressure threshold;

providing a latched third signal in response to the first and second signals;

energizing the pump in response to the third latched signal; and disabling the pump for a predetermined time interval following the monitored pressure decreasing in magnitude from above to below the high pressure threshold.

18. A system as defined by claim 1, wherein the pump control means is responsive to the output signal of the pressure sensor to raise and lower the pump pulse pressure respectively in response to a decrease and increase in the organ vascular resistance.

19. A system as defined by claim 9, wherein the pump control means is responsive to the output signal of the pressure sensor to raise and lower the pump pulse pressure respectively in response to a decrease and increase in the organ vascular resistance.

20. A method as defined by claim 16, which further includes adjusting the pump pulse pressure in accordance with the pressure of the perfusion solution in the first conduit, the pulse pressure being decreased if the pressure of the perfusion solution in the first conduit increases, and being increased if the pressure of the perfusion solution in the first conduit decreases.

* * * * *

UNITED STATES PATENT AND TRADEMARK OFFICE
CERTIFICATE OF CORRECTION

PATENT NO. :   5,326,706
DATED      :   July 5, 1994
INVENTOR(S) :  Marc J. Yland
               David Anaise It is certified that error appears in the above-indentified patent and that said Letters Patent is hereby corrected as shown below:

Column 12, Line 65,    after "5,7 and" delete "lo" and insert --10--.

Column 13, Line 19,    after "of" delete "he" and insert --the--.

Column 13, Line 53,    after "1K ohm resistor 170" insert --.--.

Signed and Sealed this

Sixth Day of September, 1994

Attest:

BRUCE LEHMAN

*Attesting Officer*             *Commissioner of Patents and Trademarks*